(12) United States Patent
Engel

(10) Patent No.: US 7,771,118 B2
(45) Date of Patent: Aug. 10, 2010

(54) METHOD AND CONFIGURATION FOR EXAMINING A MEASUREMENT OBJECT BY WAY OF INVASIVE RADIATION

(75) Inventor: Thomas Engel, Aalen-Waldhausen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 75 days.

(21) Appl. No.: 11/994,944

(22) PCT Filed: Jul. 6, 2006

(86) PCT No.: PCT/EP2006/006756
§ 371 (c)(1),
(2), (4) Date: Mar. 18, 2008

(87) PCT Pub. No.: WO2007/003444
PCT Pub. Date: Jan. 11, 2007

(65) Prior Publication Data
US 2008/0203320 A1 Aug. 28, 2008

(30) Foreign Application Priority Data
Jul. 6, 2005 (DE) .................. 10 2005 032 686

(51) Int. Cl.
*A61B 6/08* (2006.01)
*G01N 23/04* (2006.01)
(52) U.S. Cl. ........................ 378/205; 378/62

(58) Field of Classification Search ............. 378/57–59, 378/60, 61, 901, 205, 62, 207
See application file for complete search history.

(56) References Cited

U.S. PATENT DOCUMENTS

| 4,969,110 | A |   | 11/1990 | Little et al. |         |
|-----------|---|---|---------|---------------|---------|
| 6,047,041 | A | * | 4/2000  | Ellinger      | 378/58  |
| 6,739,751 | B2| * | 5/2004  | Williams      | 378/205 |

FOREIGN PATENT DOCUMENTS

| DE | 3924066 A1  | 2/1990 |
|----|-------------|--------|
| DE | 19846885 A1 | 7/2000 |

\* cited by examiner

*Primary Examiner*—Irakli Kiknadze
(74) *Attorney, Agent, or Firm*—Laurence A. Greenberg; Werner H. Stemer; Ralph E. Locher

(57) ABSTRACT

A method and an arrangement for investigation of an object to be measured (1), the object to be measured (1) being subjected to invasive radiation. An interaction of the invasive radiation from a radiation source (3) is detected by way of a radiation-sensitive sensor device (6). An anticipated detection result for the sensor device (6) is calculated from a set geometry of the object to be measured (1) and material properties by a calculation (13) and/or an anticipated detection result is determined by measurement of a standard body and the anticipated detection result is compared with an actual detection result from the sensor device (6) by a comparator device (11).

14 Claims, 2 Drawing Sheets

METHOD AND CONFIGURATION FOR EXAMINING A MEASUREMENT OBJECT BY WAY OF INVASIVE RADIATION

BACKGROUND OF THE INVENTION

Field of the Invention

The invention relates to a method and a configuration for examining a measurement object, the measurement object being exposed to invasive radiation, in particular X-radiation.

The use of invasive radiation for examining workpieces is known. In computer tomography (CT), the workpiece is, for example, arranged on a rotary table, and is transirradiated by X-radiation from various directions by rotating the rotary table into various rotational positions. The radiation attenuated by extinction in the material of the workpiece is detected by a sensor device with spatial and time resolution. A spatially three-dimensional model of the workpiece is calculated therefrom by tomographic back projection. The model respectively includes for individual volume regions the material properties for the extinction of X-radiation. DE 39 24 066 A1 describes an example for CT.

The high outlay on measurement and the tomographic back projection is disadvantageous in this mode of procedure. In particular, powerful computers and/or computer clusters are required, in the case of workpieces with more complex shapes and/or in the case of workpieces having a number of different materials. The calculation of the model (of the measurement object by the reconstruction) can last a few hours. Consequently, computer tomography is qualified in suitability for examining workpieces from mass production only to a certain extent. It is mostly possible to examine only a few specimens of a series.

It is, moreover, known to measure physical objects radiographically. DE 198 46 885 A1 describes such a method, in the case of which an object is positioned between a gamma ray source or X-ray source and a radiation sensor, and exposed to the radiation. The image of the object is digitally acquired on the radiation sensor in the form of a multiplicity of points each having an associated gray scale value, and is graphically displayed on the monitor of a computer. Dimensions of the object are calculated by means of the computer from the positions and/or gray scale values of the points registered by the radiation sensor, as well as from the relative position of the radiation source and the object with reference to the radiation sensor.

BRIEF SUMMARY OF THE INVENTION

It is an object of the present invention to specify a method and a configuration for examining a measurement object by means of invasive radiation, with the aid of which method and configuration it is possible to reduce the outlay for establishing a defect. In particular, it is still possible with acceptable outlay to examine a substantially larger fraction of workpieces from mass production for defects, tolerances and/or critical dimensions (the latter being, for example, thickness, width and/or diameter at least of parts of the workpiece).

A method for examining a measurement object is proposed, in which the measurement object is exposed to invasive radiation,
an interaction of the invasive radiation with the measurement object is detected by means of a radiation-sensitive, preferably spatially resolving sensor device,
an expected detection result of the sensor device is calculated by using a desired geometry of the measurement object and by using material properties, and/or an expected detection result is determined by measuring at least one master part, and
the expected detection result is compared with an actual detection result of the sensor device.

The actual detection result is, in particular, a direct detection result of the sensor device that has been obtained without tomographic back projection (CT). However, this does not prevent such a back projection from being carried out after the comparison.

The term invasive radiation covers radiation of any type that penetrates into the measurement object and/or passes through the measurement object. Particle radiation (for example electron radiation or positron radiation) can also be used apart from electromagnetic radiation—such as X-radiation, for example. It is also possible to use electromagnetic radiation in other wavelength regions (for example in the visible or infrared wavelength region). Again, it is possible to use secondary effects for the examination, for example in magnetic resonance (MR) technology or in the case of the excitation of energy states by electromagnetic radiation (for example luminescence). Secondary or scattered radiation can also be detected in the case of X-radiation.

In a preferred type of examination of the measurement object, use is made (as with CT) of electromagnetic radiation that passes through the measurement object and is detected on the opposite side of the radiation source by the spatially resolving sensor device. It is an advantage of this configuration that is simple by comparison with configurations that evaluate reflected radiation. By comparison with the expected detection result, it is possible to directly obtain information relating to defects in the interior of the measurement object, for example undesired cracks and cavities in the material and/or wrongly positioned shaped features such as bores and cutouts.

The desired geometry is obtained from CAD (Computer Aided Design) planning data of the measurement object, for example. The desired geometry preferably also comprises specification as to which parts of the measurement object are fabricated from which material. In particular, modern CAD systems have a data interface that is used to further process a three-dimensional model of the respective workpiece or measurement object by means of digital data processing (CAM, Computer Aided Modeling). In a preferred refinement of an inventive configuration, the configuration is connected to such an interface, or is at least configured to be connected to such an interface. Alternatively or in addition, the CAD system is part of the configuration, that is to say at least the devices required for calculating the expected detection results are part of the CAD system. The CAD system can, in addition, fulfill further tasks, for example it can have the comparing device for comparing the expected and the measured detection results. Furthermore, material properties can be included in a model of the workpiece provided by the CAD system via the interface and, for example, be respectively coded by a color assigned to a specific material or by the corresponding color value. Such models can be displayed on an image display device. It is preferably possible to produce corresponding models of the expected detection result and/or models of differences between the measured and the expected detection result.

The material properties are, in particular, the absorption coefficient(s) of the material(s) of the measurement object. Moreover, the material properties can also include how the radiation is scattered in the material and/or what is the impact of secondary effects (see above). The material properties can, for example, be determined in a separate measurement on a block made from the same material, and/or be taken from the literature. The material properties for the comparison are preferably available as a function of the various parameters, such as wavelength of the invasive radiation, for example, that can be set during the measurement of the measurement object.

In a more general formulation, it is, in particular, optionally possible, for example, depending on the desired accuracy and/or the type of interaction examined, to use a simpler or more complex description of the interaction when calculating the expected detection result. For example, it is possible in the one case to consider only the absorption of the invasive radiation in the material, and in another case also to consider the control of radiation and/or the production of secondary radiation.

It is, however, also possible to measure at least a master part of the measurement object from the same measuring device, which is also used to examine the actual measurement object. That is to say, the master part is exposed to the invasive radiation in the same way as the measurement object previously and subsequently. The measurement results from the measurement of the master part can then be used directly for the comparison. It is also possible to use combinations of the results of the measurement of a number of master parts for the comparison. In this case, it is particularly possible to measure the master part or the master parts repeatedly under different measuring conditions (for example, exposure time, direction of the radiation, type and/or wavelength of the radiation used), and to determine the comparative values. Nevertheless, when examining an instance of mass production, the outlay for the measurement of a master part is to be executed at a much lower level than the conventional tomographic back projection for each individual measurement object.

Furthermore, it is possible for the master part or master parts to be measured by means of other measuring methods than are applied when measuring the measurement object. For example, methods of the classic coordinate measurement technique (for example, optical and/or tactile determination of surface coordinates) can be used to this end. At least parts of the detection results expected can be calculated therefrom.

It is also possible to use one of these other measuring methods to select an expected detection result, a plurality of various expected detection results being available for selection. In this case, the measurement object itself can be an object for measuring with the aid of the other measuring method.

The inventive method has the advantage that the determination of the expected detection result is possible in many instances with a substantially lesser outlay than a tomographic back projection. This holds, in particular if a plurality of specimens that are intended to correspond to the same desired geometry are examined. The tomographic back projection to be executed several times in this case is opposed only by the one-off determination of the expected detection result.

Moreover, deviant expected detection results can be calculated in a simple way in particular by fixing a permitted tolerance of the material properties and/or of the desired geometry. If the measured detection result still corresponds to these deviant expected detection results (or if the detection result lies between the ideal expected detection result and the deviant expected detection result), there is still no defect present. In particular, it is respectively possible to determine therefrom a limiting value for the individual detector signals (see below).

Preferably, at least one second expected detection result is calculated, the second detection result corresponding to a state that is changed by comparison with the desired geometry and/or the expected material properties and still lies in a permissible range, and it is determined by comparing the second expected detection result with the actual detection result whether the actual detection result still lies in the permissible range.

In order to be able to compare the expected detection results with the measured ones, a registration of the coordinate systems of the desired geometry and the measuring configuration for measuring the measurement object is, or has already been, undertaken. Registration is understood as the production of a unique spatial reference which relates to the mutual position and alignment of the coordinate systems.

In particular, when carrying out the registration, prior knowledge is available in relation to the position and alignment of the measurement object during measurement, and thus with reference to the measurement system. In this way, the measured coordinate data record can already be preregistered, that is to say be registered except for a small error with reference to the coordinate system of the desired geometry. In particular, the measuring configuration can be configured mechanically to ensure that the measurement object is located in a defined position and/or alignment relative to the measuring configuration (in particular, relative to the radiation source and the sensor device), when it is in contact with a specific part or parts of the measuring configuration (for example, indicated in a mechanical hold/fit).

Moreover, it is optionally possible to carry out a correction of the registration. In this case, for example, the measured values of characteristic spatial areas of the measurement object are compared with corresponding expected measured values. If the alignment and/or position do not correspond, alleviation can be compared. For example, the sum of the squares of the errors (the error corresponds respectively to the deviation in the measured values, in particular gray scale values, for corresponding positions) of all the areas or pixels considered during correction is minimized, or the greatest errors are minimized.

In a more general formulation, a plurality of expected detection results can be calculated, each of the detection results corresponding to a different position and/or alignment of the measurement object relative to the radiation source and/or relative to the sensor device, and/or corresponding to different values of another measurement parameter. By comparing the various expected detection results with the actual detection result, it can be determined (for example, by the minimization of the squares of the errors that has been described) which of the expected detection results corresponds best to the actual detection result, and the correction of the registration can be determined therefrom. For example, at least a part of the expected detection results can respectively correspond to one of various rotational positions of the measurement object about an axis of rotation of the measuring configuration.

Before a measurement of the measurement object, it is preferred to determine and/or calculate an expected detection result and to evaluate the detection result in order to select measurement parameters when measuring the measurement object and/or in order to select a type of measurement of the measurement object. For example, it is therefore possible for measurement signals to lie in an advantageous value range of the sensor device when the measurement object is being measured. In particular, the data obtained from the measurement of the measurement object can be optimized (for example with regard to their quality, for example by virtue of the fact that the measured data lie in an optimum measurement range of the sensor device), and/or the outlay for measuring the measurement object is minimized (in particular minimization of the measuring time). Consequently, optimum planning and design of the measurement can save a great deal of time and outlay in carrying out the measurement and evaluating it.

A further advantage of the present invention consists in that only specific (selected) radiation images of the measurement object can be recorded and evaluated owing, in particular, to the planning described in the previous paragraph. For example, it is particularly informative images that are involved here. The measurement outlay can therefore be kept very low.

If it has been established in the comparison that an error is present, a complete CT examination can, moreover, optionally take place, including tomographic back projection. This has the advantage that a large number of workpieces from an instance of mass production can be examined, and that in the event of error it can reliably be established at which location of the measurement object a defect is present.

The detection result obtained from the measurement of the measurement object is preferably checked for errors by comparison with the expected detection result or results. During the error check, it is established, in particular, whether the measured detection result lies within tolerances given by the expected detection results. In this case, the error evaluation can be carried out in a spatially desired fashion with reference to a coordinate system of the measurement object and/or with reference to a coordinate system of the sensor device. For example, one or more dimensions (for example thickness, width and/or diameter at least of parts of the workpiece) are determined, and it is established whether the respective tolerance is observed.

The sensor device can also be a sensor device with a number of component sensors spaced apart from one another, the component sensors respectively again enabling a spatially resolved measurement of the invasive radiation.

For example, at least one of the component sensors, or the sensor device arranged without spatial distribution has a plurality of spatial areas, the invasive radiation striking in the individual spatial areas being capable of conversion into an independent measurement signal. The component sensors, or a sensor configuration not arranged in a spatially distributed fashion can be, for example, a matrix of radiation-sensitive semiconductor elements. In this case, both row matrices with only one row of semiconductor elements, and semiconductor matrices with sensor elements in a number of rows and columns come into consideration.

For example, the sensor device has a multiplicity of the radiation-sensitive spatial areas, and the expected detection result is prepared for the comparison with the measured detection result in such a way that a comparative value is available for each of the spatial areas. Consequently, it can be established as quickly as possible whether an error is present. In particular, a limiting value can be defined for the difference between the expected and measured detection results. If the limiting value is reached or overshot in one of the spatial areas, it is established that a defect is present in the spatial area.

In particular, the sensor signals of the sensor device can be automatically digitized such that the actual detection result is available in digitized form for comparison with the expected detection result.

The measurement object is preferably exposed to the invasive radiation from various directions and/or in various rotational positions (and, particularly, temporally one after another), and a detection result is respectively established, that is to say the results of the interaction with the measurement object are respectively detected. Particularly in the case of the passage of the invasive radiation through the measurement object, it can thus be achieved that each volume region of the measurement object is transirradiated from different directions. Each of the detection results (in particular, those established temporally one after another) can be compared with an expected detection result, and the location of a defect in the measurement object can be determined with reference to the desired geometry from deviations in the actual detection results from the expected detection results, or can at least be delimited. However, the outlay for this is substantially less than in the case of a complete tomographic back projection.

In a development of this embodiment of the method, the detection results are respectively produced as fields of detection values (such as for example, also in the case of conventional CT, with subsequent back projection), the actual detection values and the associated expected detection values respectively being compared with one another, in particular being subtracted from one another. The fields of comparative values resulting therefrom are then used to produce a spatially three-dimensional defect model of the measurement object by a tomographic back projection. A field of values is understood as a plurality of the values that are referred to a coordinate system of the measurement object or the desired geometry. In other words, the field is used to assign in each case to a plurality of spatial areas in the respective coordinate system a value, for example a gray scale value, that corresponds to an absorption of radiation. When the measurement object is transirradiated by the invasive radiation, and the correspondingly attenuated radiation is detected by the sensor device, a two-dimensional coordinate system corresponds to this whose axes run in a plane that extends approximately perpendicularly to the direction of the radiation.

This embodiment of the invention is based on the finding that, even in the output data of such a tomographic back projection (that is to say the differences in the radiation images recorded from various directions from the expected detection results), all information as to the point of the measurement object where the defect is present is available. However, the information need not be evaluated by a complicated, complete tomographic back projection.

Expressed more generally, the difference from the conventional tomographic back projection consists in that the input values for the back projection are not the measured values, but the comparative values (in particular, in each case the difference between the measured and the expected measured value of a spatial area of the sensor device). In particular, all the input values (each input value being able to correspond to a sensor element of the sensor device) that are different from the expected input value by more than a prescribed limiting value (see above) can be equated to zero. In this case, the outlay on the back projection is substantially less than in the case of the conventional back projection.

Before the comparison of the expected and the measured detection result, the measured detection result is preferably corrected with reference to the usual systematic measuring errors. In particular, the background signal (offset) is corrected (in particular, subtracted), and the gain of the measurement signal is correctly set or corrected.

In a design variant, it is possible to obtain non-spatially resolved measured values at least in subareas of the sensor device, or a spatial mean value can be determined from the measured values obtained with spatial resolution. By comparison with a corresponding expected measured value, it is possible in a particularly simple way to obtain first results relating to the presence of an error or a deviation from the desired state. For example, it is possible in this way (taking account of the weight) to measure the mean density of the measurement object and compare it with the expected value. For example, it can be established therefrom whether unexpected or undesired cavities such as shrink holes or bubbles exist in the measurement object.

Furthermore, there is proposed a configuration for examining a measurement object, in which the configuration exhibits the following:

a radiation source for producing invasive radiation, a sensor device for measuring a result of an interaction of the invasive radiation with the measurement object, a calculating device for calculating an expected detection result of the sensor device by using a desired geometry of the measurement object and by using material properties, and/or a memory device for storing an expected detection result that is or was determined by measuring at least one master part, and a comparing device that is connected to the sensor device and to the calculating device, and/or that is connected to the sensor device and the memory device, the comparing device being configured to compare the expected detection result with an actual detection result of the sensor device.

The comparing device can be connected in any suitable way to the sensor device and the calculating device. For example, the devices can be interconnected in a wireless fashion, in particular via a radiolink, optical signal connection and/or ultrasound link.

Furthermore, it is possible to provide a defect-determining device that is connected to the comparing device and is configured to establish a defect of the measurement object as a function of the result of the comparing device. In particular, a defect of the measurement object is present whenever a significant deviation, overshooting a delimiting value, has been determined between the expected detection result and the actual detection result.

In particular, the measuring configuration can be part of a production plant for mass producing workpieces, individual workpieces or all of the workpieces produced being measured with the aid of a measuring configuration, and it is, or can be, established in accordance with the described method whether a defect is present. This serves, in particular, to monitor and ensure quality and production. In this case, a measuring station of the measuring configuration, on which the workpiece can be examined by means of the invasive radiation, can lie directly on a path that must be traversed by all the workpieces produced (it then optionally also being possible to examine only selected workpieces, or to examine all the workpieces), and/or the workpieces to be examined with the aid of the measuring configuration can automatically be segregated from the production line and transported to the measuring configuration.

Furthermore, the scope of the invention includes a computer program that, when run on a computer or a computer network, executes at least those parts of the inventive method in one of its refinements that relate to the examination of the expected detection result and/or the evaluation of the measured detection result and comparison thereof.

Furthermore, the scope of the invention includes a computer program with program code means for carrying out the method, defined in the preceding paragraph, in one of its refinements when the program is executed on a computer or computer network. In particular, the program code means can be stored on a computer-readable data medium.

Moreover, the scope of the invention includes a data medium on which there is stored a data structure that can execute the method in one of its refinements after having been loaded into a user and/or main memory of a computer or computer network.

Also included in the scope of the invention is a computer program product having program code means stored on a machine-readable medium, in order to carry out the method in one of its refinements when the program is executed on a computer or computer network.

The program as commercial product is understood here under the term computer program product. It can fundamentally be present in any desired form such as, for example, on paper or a computer-readable data medium and can, in particular, be distributed over a data transmission network.

The invention will now be described with reference to the drawing with the aid of exemplary embodiments.

BRIEF DESCRIPTION OF THE SEVERAL VIEWS OF THE DRAWING

However, the invention is not restricted to the exemplary embodiments. Individual features of the following description or any combinations thereof can be combined with the refinements of the invention previously described. In the individual figures of the drawing.

DESCRIPTION OF THE INVENTION

Figure 1:
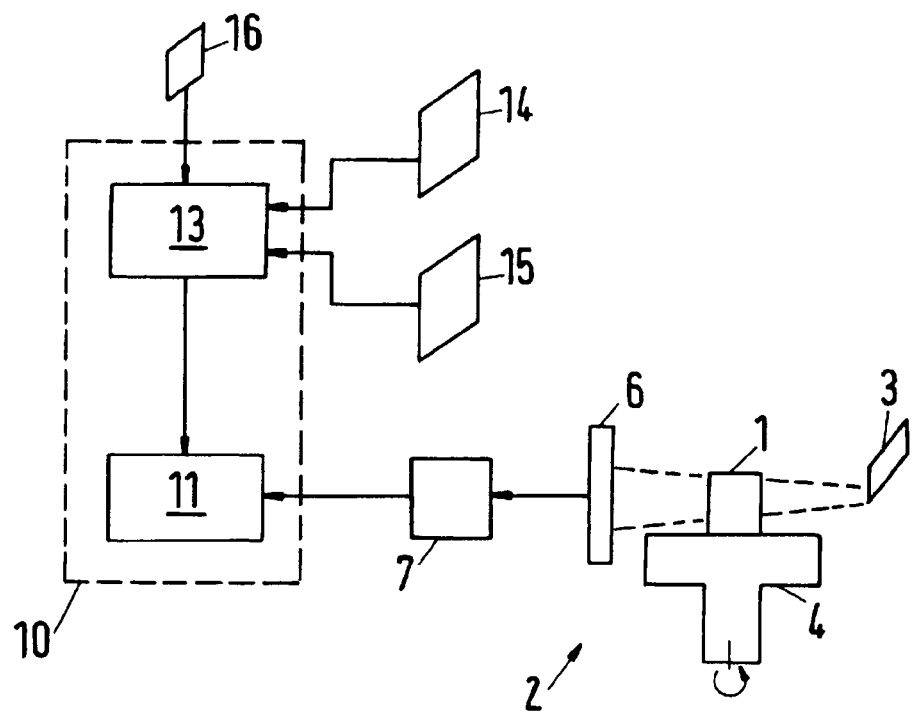
FIG. 1 shows a configuration for examining a measurement object by means of invasive radiation.

The configuration illustrated in FIG. 1 has a measuring device 2 that can be used to measure a measurement object 1 by means of invasive radiation.

The measuring device 2 has, for example, an X-ray source 3 for producing X-radiation and for directing a conical X-ray beam onto the measurement object 1. The bounds of the radiation beam are illustrated in FIG. 1 by dashed lines. The X-radiation passes through the measurement object 1 and strikes a sensor device 6 with attenuated intensity. The main reason for the attenuation of the X-radiation is the absorption in the material of the measurement object 1. Furthermore, the X-radiation is scattered in the measurement object 1. In this process, a fraction of the scattered radiation passes once again onto the sensor device 6.

In the exemplary embodiment, the sensor device 6 comprises an n×m matrix of sensor elements that are sensitive to the X-radiation. Here, n, m are positive integers, and denote the number of rows and columns in which the individual sensor elements are arranged. Depending on the sum (quantity) of the incident radiation or on the intensity of the incident radiation, each of the sensor elements supplies a measurement signal that is further processed by components (considered in more detail later) downstream in terms of signaling.

In the exemplary embodiment, the measurement object 1 is arranged on a rotary table 4 that is rotated about its vertical axis during the measurement operation, as is indicated by a corresponding arrow in FIG. 1.

Consequently, the sensor device 6 supplies spatially two-dimensional X-ray images of various rotational positions of the measurement object 1. Corresponding output signals of the sensor device 6 are transmitted via a signal connection to a correcting device 7 which carries out a background and gain correction for each individual one of the signals of the sensor elements. On the output side, the correcting device 7 is connected to a comparing device 11 that, in turn, is a component of an evaluation device 10. Via the corresponding connection between the correcting device 7 and the comparing device 11, the corrected sensor signals are transmitted to the comparing device 11, specifically in a spatially resolved fashion (corresponding to the matrix elements of the sensor device 6) and in a time resolved fashion (corresponding to the X-ray images recorded in the various rotational positions of the rotary table 4).

A data record with geometrical data of a desired geometry of the measurement object 1 is denoted in FIG. 1 by the reference numeral 14. Desired geometry is understood as meaning that the measurement object 1 is to exhibit the corresponding geometry, that is to say shape. However, this is frequently not the case in practice, since during production of the measurement object 1 (at the surface and/or in the measurement object) it is possible for defects to have occurred, or the shape of the measurement object 1 can deviate from the desired geometry for other reasons, for example on the basis of damage or wear.

Material property data of the desired state of the measurement object 1 are denoted by the reference numeral 15. The material property data 15 preferably also include the reference to the respective location in the coordinate system of the desired geometry at which the respective material property is present. In particular, the material properties are the absorption coefficient of the respective material for the X-radiation used in the measuring device 2, and the effect cross section for the scattering of this X-radiation. In this case, if appropriate, when the measurement object 1 consists of various materials, the material properties are specified for all the materials of the desired state of the measurement object 1.

The geometrical data 14 and the material property data 15 are input data for a calculating device 13 that is part of the evaluation device 10. In this configuration, the evaluation device 10 is not necessarily a unit of the equipment. Rather, the calculating device 13 can be arranged separately from the comparing device 11 and can, for example, fulfill its function in advance, that is to say before the first measurement is executed such that only a corresponding calculation result is present and is used by the comparing device 11. The calculating device 13 is configured to use the geometric data and the material property data to calculate expected measured values of the sensor elements of the sensor device 6 under the assumption that the measurement object 1 corresponds to the desired geometry and the desired state. In this process, moreover, it is optionally possible to take account of a tolerance of the desired geometry and the material properties. In order to be able to calculate the expected measured values correctly for the desired state and the desired geometry, measurement parameter data 16 are also provided as input data of the calculating device 13. The measurement parameter data include information relating to properties of the measurement, in particular spatial resolution of the sensor device 6, exposure time (that is to say a radiation time for the recording of an individual X-ray image by the sensor device 6), energy and wavelength or frequency and/or the corresponding distribution of energy, wavelength or frequency in the X-radiation used, geometry of the configuration of the X-ray source 3 and the sensor device 6, opening angle of the X-ray source 3, and size and intensity distribution of the radiation cone that emanates from the X-ray source 3, and/or further parameters that may be required for a particular measuring configuration in order to be able to predict the expected measurement signal of each individual sensor element for the desired geometry and the desired state.

The measurement parameter data can optionally be available for a plurality of possible measurements of the measurement object, and the calculating device can carry out the calculation of the expected detection result for each case of the various possible measurements.

Apart from the particular exemplary embodiment of the invention, it is also basically possible in the case of individual or a number of the measurement parameters mentioned in this description, or other measurement parameters, to carry out measurements of the measurement object with spatial variation (referred to the location in the measurement object or to the location of the sensor device) and/or with temporal variation. In particular, it is possible in the case of the above-described planning of the measurement also to optimize the variation of the measurement parameter or parameters taking account of expected measurement results.

Results of the calculating device 13 are fed to the comparing device 11 via a corresponding signal line. Alternatively, or in addition, the results are stored in a data memory (not illustrated in FIG. 1) from which the comparing device 11 can call up the results as required. The calculating device 13 and the comparing device 11 can in each case be a cluster of powerful computers. In most cases, it is sufficient for the relatively quick and easily executable computing operations of the comparing device 11 when the comparing device is implemented by a single commercially available personal computer (PC) and the corresponding software. It is only in the case of an additional back projection after a defect has been established (see above in the general part of the description) that more powerful computing devices are required or that such powerful devices are advantageous in order to obtain the result in a more reasonable time.

In particular, the geometric data 14 and the material property data 15 are data in three-dimensional space that are, for example, referred to an object-inherent coordinate system of the desired geometry. Thus, the data can respectively be referred, for example, to the three coordinates of a Cartesian coordinate system whose origin is fixed with reference to the object. In the case of objects having different materials, it is optionally additionally possible for the information as to which material region is to be produced from which material to be contained in the geometric data. This additional information is, for example, likewise assigned to the respective coordinate point or volume element in the coordinate system. The calculating device can, for example, compile therefrom a three-dimensional model of the desired object from which the expected measured values of the sensor elements can be determined for each case of the configuration of the measurement object, the radiation source and the sensor device.

Leaving aside the particular exemplary embodiment, it is a further advantage of the invention that it is also possible to make optimum use of the measurement ranges of the measuring device because of the fact that measured values expected first of all are calculated. For example, it can be determined first of all whether an expected measured value will have a high or a low measuring error, for example because the measured value is too small in relation to the background value to be subtracted, or is sufficiently large. Consequently, the exposure time can be adapted, for example. This evaluation as to whether the measuring device is being driven optimally can be performed, for example, automatically by evaluating the calculation results of the calculating device. In an extension of this idea, it is also possible to undertake multiple exposures with, for example, various exposure times, and/or to use radiation with different wavelengths. It is also possible, alternatively or in addition, to use other types of invasive radiation and/or to combine various types, for example particle beams and X-rays, or radiation of various colors in the case of measurement objects that can pass visible radiation. Moreover, it is thus correspondingly possible to preplan and optimize measurements with the aid of various detectors. For example, a sensor device as illustrated in FIG. 1 can be provided for measuring the extinction when the measurement object is transirradiated, and it is also additionally possible to provide a detector for measuring the scattered radiation and/or measuring secondary effects. Again, a sensor device can be provided for measuring radiation that is reflected and/or scattered at surfaces of the measurement object.

A further advantage of the invention resides in the fact that a relatively high outlay in which, for example, the complicated physical processes described in the previous paragraph can be taken into account, can be expended in order to calculate the expected measurement results. Consequently, the calculation result can be very accurate. The result of the calculating device is preferably checked first of all, or repeatedly after the measurement of measurement objects, by measuring a master part that corresponds as exactly as possible to the desired geometry and the desired state.

The previously mentioned optimization of the planning of the measurement by evaluation of the calculation results of the calculating device is particularly advantageous when the measurement object has two or more different materials that have only slightly different absorption or scattering properties, at least for a specific invasive radiation. In particular, when yet a third material having clearly different radiation properties is present, it could be, on the other hand, that the difference between the two materials which are similar with regard to their radiation properties cannot be sufficiently detected in a measurement with the aid of only one type of radiation and a single exposure.

A further means for optimizing measurement that can be applied independently of or in combination with the previously described measures is to set the gain of the detector signals as a function of the calculation result of the calculating device (that is to say as a function of the expected measured values).

The previously mentioned measurement parameters and/or further measurement parameters, such as information relating to the uniformity of the detection properties of the sensor elements, for example, of the measuring device are preferably determined and transmitted to the comparing device. In this way, the associated calculation result can be selected if a number of calculation results are present. Moreover, the comparing device and/or the calculating device can monitor whether the results of the calculating device are suitable for the measuring method actually executed, and whether a rational comparison can be carried out.

The optimization of the measurement parameters as a function of the result of the calculating device can also be undertaken individually and variously for different orientations or rotational positions (in general for different configurations of the measurement object relative to the radiation source and/or relative to the sensor device). Furthermore, it is possible to select from the plurality of calculation results one or more configurations of the measurement object with the aid of which the desired examination can be carried out most quickly and/or most clearly. For example, there are particular configurations in which a defect can be detected particularly well.

A further advantageous refinement of the inventive method relates to the evaluation of the quality of the measurement object in the event of deviations from the desired state and/or the desired geometry. The calculating device can undertake the calculation of the expected measured values for different deviations from the desired state and the desired geometry, and the corresponding individual calculation results can be compared with the measurement result. In particular, it is possible previously to simulate frequently occurring or particularly expected defects of the measurement object and to calculate a corresponding expected measurement result. In this way, it is possible to determine which defect is present and/or how strongly the quality is impaired by determining to which of the calculated measurement results the measurement result actually obtained from the measurement is most similar. It is also optionally possible to determine therefrom an evaluation measure on an evaluation scale, in which case, for example, there is at one end of the scale a complete correspondence between the desired state and desired geometry, on the one hand, and the measurement object, on the other hand, and the degree of the deviations intensifying over the scale.

Figure 2:
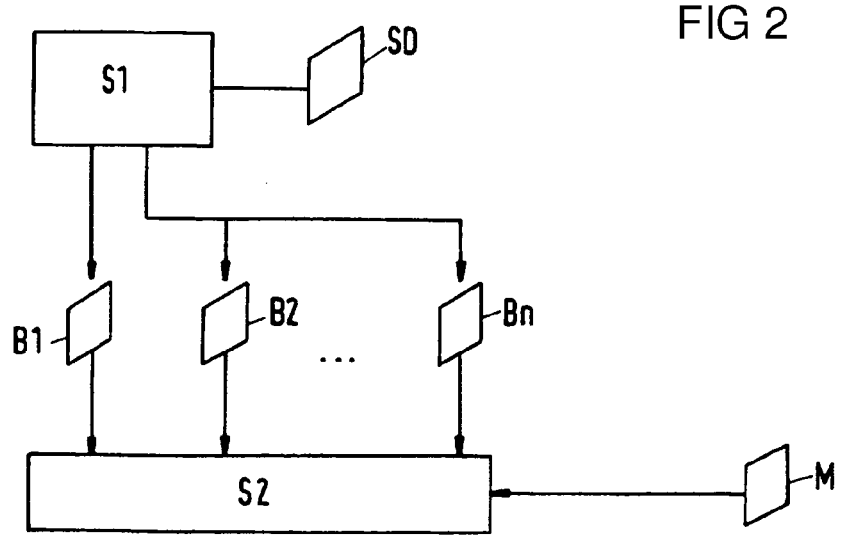
FIG. 2 shows a schematic flow diagram for illustrating an exemplary embodiment in which a plurality of expected detection results are calculated and evaluated.

FIG. 2 shows a corresponding exemplary embodiment. Desired data SD are used in step S1 to calculate various calculation results $B1, B2, \ldots Bn$ having different deviations from the desired state and the desired geometry. Here, n is a positive integer, and the calculation results $B1, B2, \ldots Bn$ are ordered in accordance with the degree of deviation from the desired state and the desired geometry. The calculation result B corresponds in this case to the ideal state. The calculation result Bn already corresponds to a no longer acceptable quality, since the deviation from the ideal state is very large.

In step S2, the result of a measurement of the measurement object, for example in the measuring configuration 2 described with the aid of FIG. 1, is now compared with the calculation results B. The calculation result B which best corresponds is determined, and the corresponding quality (for example "3" for a correspondence with the calculation result B3) is output. When comparing the calculation results B with the measurement result M, for example, that calculation result B whose sum of the squares of the deviations in the individual measured values is minimal is determined. In this case, the individual measured values are understood as the respective expected measured value and the associated calculated measured value for an individual sensor element (or for an individual point or surface area of the spatially resolving sensor device).

A further advantage of the inventive method consists in the fact that the actual measurement of the measurement object can be restricted to a low number of rotational positions or relative positions to the radiation source and the sensor device. In particular, (as already indicated above) it is possible, in turn, to consider the calculation result of the calculating device in order to select those configurations of the measurement object relative to the radiation source and the sensor device that are particularly informative. Relative configurations in which specific expected defects are to be detected most effectively are selected, for example. The position of a bore inside the measurement object in a specific rotational position can thus, for example, be detected most effectively.

The aim is to examine an exemplary embodiment of the calculation of the expected measured value for an individual sensor element. To this end, reference is made to FIG. 3. A radiation source 3 is illustrated in the figure ideally as being punctiform. The invasive radiation emanating from the radiation source 3 penetrates the measurement object 1 and strikes the sensor device 6. The measurement object 1, the radiation source 3 and the sensor device 6 can be the same objects or devices as in FIG. 1, or other objects or devices.

The sensor device 6 has a plurality of sensor elements SE that are denoted by SE1, SE2, SE3, . . . . The measurement object 1 has a plurality of projections V1, V2, V3. The radiation emanating from the radiation source 3, which strikes the sensor element SE2 with linear propagation of radiation, penetrates only the projections V1, V2, but not the main region, lying therebelow, or the projection V3 of the measurement object 1. A path integral is calculated in order to calculate the measured value of the sensor element SE2 that is based on linear propagation of radiation and absorption of radiation in the measurement object 1. In the special case of a workpiece made from a single, homogeneous material, integration yields the absorption law:

$$I = I0 * \exp(-\mu * x) \quad \text{(Equation 1).}$$

Here, I denotes the radiation intensity striking the sensor element in a given time interval, I0 denotes the radiation emitted by the radiation source in the time interval in the direction of the sensor element, exp denotes the exponential function with the base e (Euler number), x denotes the spatial variable along the propagation path of the radiation, and μ denotes the absorption coefficient for the absorption of the radiation in the material.

Figure 3:
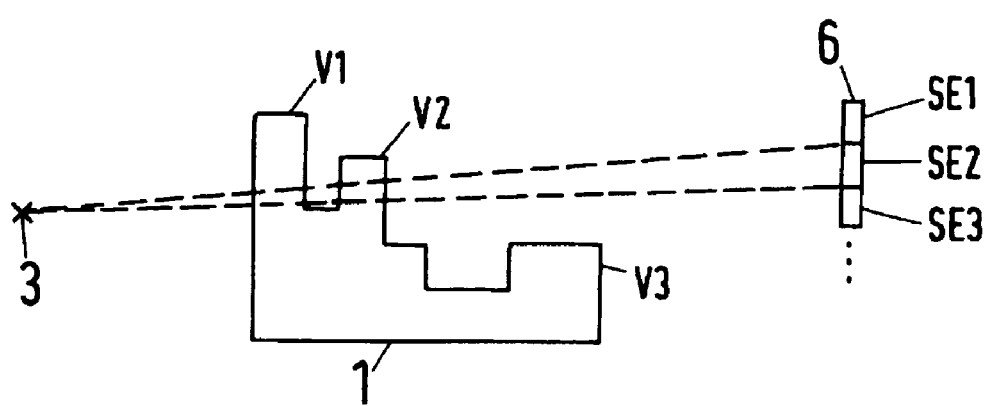
FIG. 3 shows a simplified illustration for illustrating the calculation of an expected detection result.

The integration that leads to equation 1 is executed in the example of FIG. 3 only over the width of the projections V1, V2. In practice, this can be achieved by virtue of the fact that a numerical integration method is carried out over the entire path length of the radiation, and the absorption coefficient for the regions of the radiation path between the radiation source 3 and the sensor element SE2 that lie outside the projections is set to zero.

It suffices for most cases when account is taken only of the absorption of X-radiation, particularly when a greater spacing is observed between the sensor device and the measurement object such that the effects to be blamed on scattering in the measurement object are small.

The invention claimed is:

1. A method for examining a measurement object, which comprises:
exposing the measurement object to invasive radiation;
detecting an interaction of the invasive radiation by way of a radiation-sensitive sensor device;
calculating expected detection results of the sensor device by using a setpoint geometry of the measurement object and by using material properties,
wherein each of the expected detection results corresponds to one of a different position and a different alignment of the measurement object relative to at least one of the radiation source and the sensor device;
comparing the expected detection results with an actual detection result for determining which of the expected detection results corresponds best with the actual detection result; and
deriving therefrom information relating to at least one of the position and/or alignment of the measurement object relative to the radiation source and/or relative to the sensor device.

2. The method according to claim 1, which comprises automatically digitizing the sensor signals of the sensor device to render available the actual detection result in digitized form for comparison with the expected detection results.

3. The method according to claim 1, which comprises exposing the measurement object to the invasive radiation from various directions and/or in various rotational positions and establishing respective detection results, comparing each of the detection results with an expected detection result, and determining a location of a defect in the measurement object from deviations between the actual detection results and the expected detection results.

4. The method according to claim 3, which comprises respectively producing the detection results as fields of detection values, comparing the actual detection values and the associated expected detection values respectively with one another, and generating a spatially three-dimensional defect model of the measurement object from comparative values resulting therefrom by way of a tomographic back projection.

5. The method according to claim 4, wherein the step of comparing the actual detection values and the associated expected detection values with one another comprises subtracting the values from one another.

6. The method according to claim 1, which comprises implementing the measurement steps in a mass production system and using prior measurements of prior measurement objects in a calibration and initialization of a current measurement of a current measurement object.

7. The method according to claim 1, wherein:
the expected detection results also correspond to different values of a measurement parameter of a measurement device with which the measurement object is measured, and the measurement parameter is selected from the group consisting of a wavelength of the invasive radiation, a spatial resolution of the sensor device, exposure time to the invasive radiation, energy of the radiation, frequency of the radiation, frequency distribution in the radiation, and an energy distribution in the radiation; and
the step of comparing the expected detection results with the actual detection result is used to derive information relating to a value of the measurement parameter.

8. The method according to claim 7, wherein the measurement parameter is selected from the group consisting of a wavelength of the invasive radiation, a spatial resolution of the sensor device, an exposure time, an irradiation time for the recording of an individual X-ray image by the sensor device, energy and/or wavelength or frequency and/or the corresponding distribution of energy, wavelength or frequency of the X-radiation used, geometry of the arrangement of the X-ray source and of the sensor device, opening angle of the X-ray source and/or size and intensity distribution of a radiation cone emanating from the X-ray source.

9. A method for examining a measurement object, which comprises:
exposing the measurement object to invasive radiation;
detecting an interaction of the invasive radiation by way of a radiation-sensitive sensor device;
calculating expected detection results of the sensor device by using a setpoint geometry of the measurement object and by using material properties, wherein each of the expected detection results corresponds to one of a different position and a different alignment of the measurement object relative to at least one of the radiation source and the sensor device;
comparing the expected detection results with an actual detection result for determining which of the expected detection results corresponds best with the actual detection result; and
deriving therefrom information relating to at least one of the position and/or alignment of the measurement object relative to the radiation source and/or relative to the sensor device;
wherein the sensor device has a multiplicity of separate spatial areas, and wherein invasive radiation striking in the individual spatial areas is converted into an independent measurement signal, and wherein an expected detection result is produced for each of the spatial areas and compared with a measured detection result produced from the measurement signal of the spatial area.

10. The method according to claim 1, which comprises, prior to measuring the measurement object, calculating an expected detection result and evaluating the expected detection result in order to select measurement parameters for measuring the measurement object and/or to select a type of measurement of the measurement object.

11. The method according to claim 10, which comprises calculating at least one second expected detection result, the second detection result corresponding to a state that is changed by comparison with the desired geometry and/or the expected material properties and still lies within a permissible range, and determining whether or not the actual detection result still lies in the permissible range by comparing the second expected detection result with the actual detection result.

12. A configuration for examining a measurement object, the configuration comprising:
   a radiation source for producing invasive radiation;
   a sensor device for measuring a result of an interaction of the invasive radiation with the measurement object;
   a calculating device for calculating a plurality of expected detection results of said sensor device by using a desired geometry of the measurement object and by using material properties, each of the expected detection results corresponding to one of a different position and/or and a different alignment of the measurement object relative to at least one of the radiation source and the sensor device;
   a comparing device connected to said sensor device and to said calculating device and configured to compare the plurality of expected detection results with the actual detection result;
   said comparing device determining which of the expected detection results corresponds best to the actual detection result of the sensor device in order to derive therefrom information relating to the position and/or alignment of the measurement object relative to the radiation source and/or relative to the sensor device;
   wherein the sensor device has a multiplicity of separate spatial areas, and wherein invasive radiation striking in the individual spatial areas is converted into an independent measurement signal, and wherein an expected detection result is produced for each of the spatial areas and compared with a measured detection result produced from the measurement signal of the spatial area.

13. The configuration according to claim 12, wherein:
   each of the expected detection results corresponds to different values of another measurement parameter, and the other measurement parameter is a measurement parameter of a measuring configuration for measuring the measurement object; and
   information relating to a value of the other measurement parameter is derived from the comparison between the plurality of expected detection results with the actual detection result.

14. The configuration according to claim 13, wherein the other measurement parameter is selected from the group consisting of a wavelength of the invasive radiation, spatial resolution of the sensor device, exposure time, that is to say irradiation time for the recording of an individual X-ray image by the sensor device, energy and/or wavelength or frequency and/or the corresponding distribution of energy, wavelength or frequency of the X-radiation used, geometry of the arrangement of the X-ray source and of the sensor device, opening angle of the X-ray source and/or size and intensity distribution of the radiation cone that emanates from the X-ray source, information relating to the uniformity of the detection properties of sensor elements.

* * * * *